(12) United States Patent
Albrecht et al.

(10) Patent No.: US 7,226,454 B2
(45) Date of Patent: Jun. 5, 2007

(54) WARMING DEVICE WITH VARIED PERMEABILITY

(75) Inventors: Mark Christopher Albrecht, Chanhassen, MN (US); Andrew Jacob McGregor, Minneapolis, MN (US); Thomas P. Anderson, Savage, MN (US); Gary L. Hansen, Eden Prairie, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

(21) Appl. No.: 11/005,883

(22) Filed: Dec. 7, 2004

(65) Prior Publication Data

US 2006/0122671 A1    Jun. 8, 2006

(51) Int. Cl.
*A61F 7/02*    (2006.01)
(52) U.S. Cl. .................................. 606/104; 607/108
(58) Field of Classification Search ............. 607/104, 607/96, 108, 114; 2/114, DIG. 1
See application file for complete search history.

(56) References Cited

U.S. PATENT DOCUMENTS

| | | | | |
|---|---|---|---|---|
| 2,573,414 A | 10/1951 | Dunn | ........................ | 128/144 |
| 2,826,758 A | 3/1958 | Kahn | ........................ | 2/81 |
| 3,468,299 A | 9/1969 | D'Amato | ........................ | 126/204 |
| 3,610,323 A | 10/1971 | Troyer | ........................ | 165/46 |
| 3,855,635 A | 12/1974 | Ramirez | ........................ | 2/114 |
| 3,911,499 A | 10/1975 | Benevento et al. | ........................ | 2/114 |
| 3,950,789 A | 4/1976 | Konz et al. | ........................ | 2/93 |
| 4,055,173 A | 10/1977 | Knab | ........................ | 128/139 |
| 4,146,933 A | 4/1979 | Jenkins et al. | ........................ | 2/2 |
| 4,369,528 A | 1/1983 | Vest et al. | ........................ | 2/69 |
| 4,494,248 A | 1/1985 | Holder | ........................ | 2/69 |
| 4,524,463 A | 6/1985 | Ogden | ........................ | 2/105 |
| 4,558,468 A | 12/1985 | Landry et al. | ........................ | 2/51 |
| 4,578,825 A | 4/1986 | Vote | ........................ | 2/114 |
| 4,587,671 A | 5/1986 | Rodriguez, Jr. et al. | ........................ | 2/69 |
| 4,651,727 A | 3/1987 | Howorth | ........................ | 128/201.23 |
| 4,653,120 A | 3/1987 | Leaf | ........................ | 2/114 |
| 4,787,101 A | 11/1988 | Feinberg | ........................ | 2/105 |
| 4,914,752 A | 4/1990 | Hinson et al. | ........................ | 2/2 |
| 4,964,282 A | 10/1990 | Wagner | ........................ | 62/259.3 |
| 5,062,424 A | 11/1991 | Hooker | ........................ | 128/379 |
| 5,255,390 A | 10/1993 | Gross et al. | ........................ | 2/2 |
| 5,304,213 A | 4/1994 | Berke et al. | ........................ | 607/104 |
| 5,360,439 A | 11/1994 | Dickerhoff et al. | ........................ | 607/104 |

(Continued)

FOREIGN PATENT DOCUMENTS

GB            475811          11/1937

(Continued)

OTHER PUBLICATIONS

Augustine et al., International Publication No. WO 2003/086500 A3, Oct. 23, 2003.*

(Continued)

*Primary Examiner*—Roy D. Gibson
(74) *Attorney, Agent, or Firm*—Incaplaw; Terrance A. Meador

(57) ABSTRACT

A warming device includes a clinical garment having an inside surface supporting a convective apparatus with separately-inflatable sections, each adapted to enable a particular mode of warming. Each section has a surface or region with a permeability that varies from the permeability of a surface or region in another section.

22 Claims, 5 Drawing Sheets

U.S. PATENT DOCUMENTS

| | | | |
|---|---|---|---|
| 5,367,710 A | 11/1994 | Karmin | 2/114 |
| 5,411,541 A | 5/1995 | Bell et al. | 607/104 |
| 5,443,488 A | 8/1995 | Namenye et al. | 607/104 |
| 5,572,742 A | 11/1996 | McFadden | 2/114 |
| 5,575,006 A | 11/1996 | Wolfe | 2/114 |
| 5,611,087 A | 3/1997 | Adkins | 2/114 |
| 5,620,482 A | 4/1997 | Augustine et al. | 607/107 |
| 5,675,848 A * | 10/1997 | Kappel | 5/482 |
| 5,697,963 A | 12/1997 | Augustine | 607/108 |
| 5,785,716 A | 7/1998 | Bayron | 607/108 |
| 5,891,187 A | 4/1999 | Winthrop et al. | 607/96 |
| 5,970,519 A | 10/1999 | Weber | 2/81 |
| 5,974,605 A | 11/1999 | Dickerhoff et al. | 5/421 |
| 6,049,907 A | 4/2000 | Palomo | 2/51 |
| 6,154,883 A | 12/2000 | Spann et al. | 2/69 |
| 6,216,270 B1 | 4/2001 | Moquin et al. | 2/69 |
| 6,235,659 B1 | 5/2001 | McAmish et al. | 442/79 |
| 6,378,136 B2 | 4/2002 | Matsushita | 2/114 |
| 6,484,321 B1 | 11/2002 | Shamam | 2/114 |
| 6,511,501 B1 | 1/2003 | Augustine et al. | 607/96 |
| 6,524,332 B1 | 2/2003 | Augustine et al. | 607/107 |
| 6,571,574 B1 | 6/2003 | Blackstone | 62/420 |
| 6,596,019 B2 | 7/2003 | Turner et al. | 607/108 |
| 6,647,552 B1 | 11/2003 | Hogan | 2/114 |
| 6,694,522 B1 | 2/2004 | Neal | 2/114 |
| 6,792,622 B2 | 9/2004 | Graves | 2/114 |
| 6,799,332 B2 | 10/2004 | Hatton | 2/114 |
| 6,851,125 B2 | 2/2005 | Fujikawa et al. | 2/51 |
| 6,876,884 B2 | 4/2005 | Hansen et al. | 607/98 |
| 7,001,416 B2 | 2/2006 | Augustine et al. | 607/104 |
| 2005/0015127 A1 | 1/2005 | Augustine et al. | 607/104 |
| 2005/0143796 A1 | 6/2005 | Augustine et al. | 607/104 |
| 2006/0047332 A1 | 3/2006 | Malmberg et al. | 607/104 |
| 2006/0122671 A1 | 6/2006 | Albrecht et al. | 607/104 |
| 2006/0122672 A1 | 6/2006 | Anderson | 607/104 |
| 2006/0184216 A1 | 8/2006 | Van Duren | 607/104 |
| 2006/0184217 A1 | 8/2006 | Van Duren | 607/104 |
| 2006/0184218 A1 | 8/2006 | Bieberich | 607/104 |

FOREIGN PATENT DOCUMENTS

| | | |
|---|---|---|
| GB | 1 462 033 | 1/1977 |
| SE | 525 415 | 2/2005 |
| WO | WO 97/14381 | 4/1997 |
| WO | WO 98/48652 | 11/1998 |
| WO | WO 00/62726 | 10/2000 |
| WO | WO 2003/086500 A3 | 10/2003 |
| WO | WO 2003/106897 A3 | 12/2003 |
| WO | WO 2004/004500 A1 | 1/2004 |
| WO | WO 2006/010170 A1 | 2/2006 |
| WO | WO 2006/062910 A1 | 6/2006 |
| WO | WO 2006/063027 A1 | 6/2006 |
| WO | WO 2006/086587 A1 | 8/2006 |

OTHER PUBLICATIONS

International Publication No. Wo 2003/086500 A3 (PCT) Oct. 23, 2003.

EPO Examination Report mailed Oct. 24, 2006, in EP03719690.4-1526, EP Regional Phase of PCT/US2003/11128 (published as WO/2003/086500).

P.O. Fanger, Thermal Comfort: Analysis and Applications in Environmental Engineering, Danish Technical Press, 1970, pp. 5-67.

C.B. Mahony & J. Odom, Maintaining intraoperative normothermia: A meta-analysis of outcomes with costs. *AANA Journal.* Apr. 1999. vol. 67, No. 2: 155-164.

Porta-Chill—The Portable Air-Chiller-Brochure, http://www.portachil.com/, Dec. 3, 2002.

International Search Report in PCT/US2006/004644, mailed Dec. 18, 2006 (Dec. 18, 2006).

Written Opinion of the International Searching Authority (EPO) in PCT/US2006/004644, mailed Dec. 18, 2006 (Dec. 18, 2006).

International Search Report in PCT/US2006/041028, mailed Feb. 20, 2007 (Feb. 20, 2007).

Written Opinion of the International Searching Authority (EPO) in PCT/US2006/041028, mailed Feb. 20, 2007 (Feb. 20 2007).

* cited by examiner

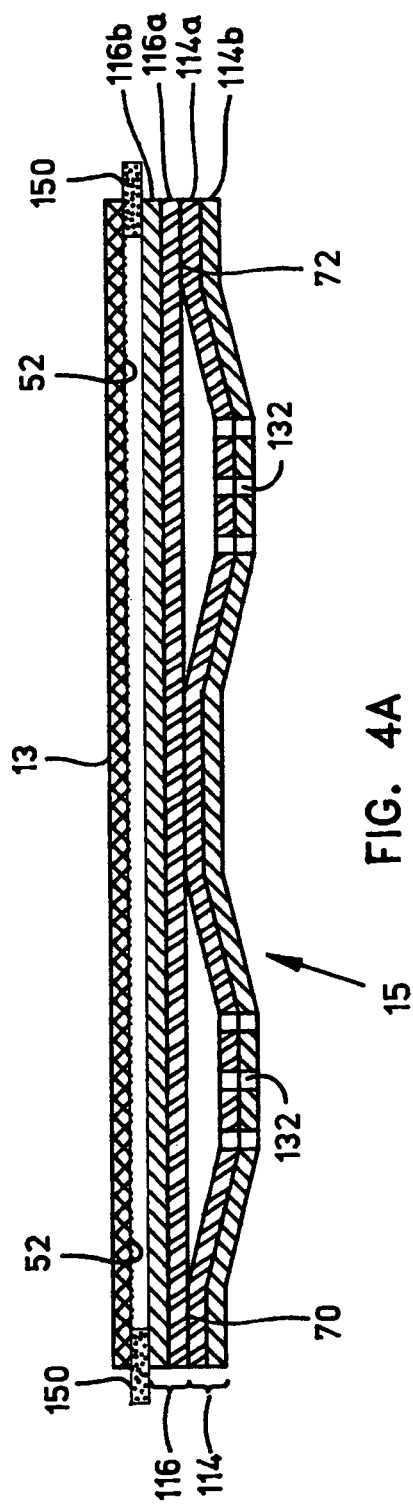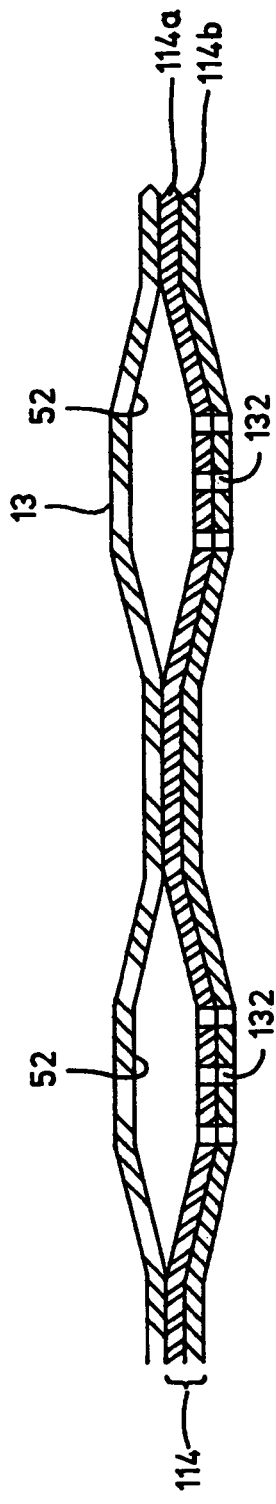
FIG. 4A
FIG. 4B

WARMING DEVICE WITH VARIED PERMEABILITY

RELATED APPLICATIONS

This application contains subject matter related to the subject matter of the following patent applications, all commonly owned herewith:

Patent Cooperation Treaty (PCT) Application No. PCT/US03/11128, filed Apr. 10, 2003, entitled "Patient Comfort Apparatus and System", and published on Oct. 23, 2003 under Publication No. WO 03/086500;

PCT Application No. PCT/US2005/025355, filed Jul. 18, 2005, entitled "Perioperative Warming Device", and published on Feb. 23, 2006 under Publication No. WO 2006/020170;

PCT Application No. PCT/US2005/043968, filed Dec. 6, 2005, entitled "Warming Device with Varied Permeability", and published on Jun. 15, 2006 under Publication No. WO 2006/062910;

PCT Application No. PCT/US2005/044214, filed Dec. 6, 2005, entitled "Warming Device", and published on Jun. 15, 2006 under Publication No. WO 2006/063027;

PCT Application No. PCT/US2006/004644, filed Feb. 9, 2006, entitled "Warming Device for Perioperative Use", and published on Aug. 17, 2006 under Publication No. WO2006/086587;

PCT Application No. PCT/US/2006/41028, filed Oct. 19, 2006, entitled Multifunction Warming Device for Perioperative Use;

U.S. patent application Ser. No. 10/411,865, filed Apr. 10, 2003, entitled "Patient Comfort Apparatus and System", and published on Oct. 16, 2003 under Publication No. U.S. 2003/0195596, now US Patent No. 7,001,416;

U.S. patent application Ser. No. 10/895,672, filed Jul. 21, 2004, entitled "Perioperative Warming Device", now abandoned, published on Jan. 20, 2005, under Publication No. U.S. 2005/0015127;

U.S. patent application Ser. No. 10/508,319, filed Sep. 20, 2004, entitled "Patient Comfort Apparatus and System", and published on Jun. 30, 2005 under Publication No. US 2005/0143796;

U.S. patent application Ser. No. 11/006,491, filed Dec. 7, 2004, entitled "Warming Device", and published on Jun. 8, 2006 under Publication No. U.S. 2006/0122672;

U.S. patent application Ser. No. 11/057,396, filed Feb. 11, 2005, entitled "Perioperative Warming Device", and published on Aug. 17, 2006 under Publication No. U.S.2006/0184215;

U.S. patent application Ser. No. 11/057,397, filed Feb. 11, 2005, entitled "Thermal Blanket for Warming the Limbs", and published on Aug. 17, 2006 under Publication No. U.S. 2006/0184216;

U.S. patent application Ser. No. 11/057,403, filed Feb. 11, 2005, entitled "Warming Device for Perioperative Use", and published on Aug. 17, 2006 under Publication No. U.S. 2006/0184217;

U.S. patent application Ser. No. 11/057,404, filed Feb. 11, 2005, entitled "Clinical Garment for Comfort Warming and Prewarming", and published on Aug. 17, 2006 under Publication No. U.S. 2006/0184218;

U.S. patent application Ser. No. 11/260,706, filed Oct. 27, 2005, entitled "Patient Comfort Apparatus and System", and published on Mar. 9, 2006 under Publication No. U.S. 2005/0052853;

U.S. patent application Ser. No. 11/363,136, filed Feb. 27, 2006, entitled "Forced Air Warming Unit", and published on Jul. 6, 2006 under Publication No. U.S. 2006/0147320;

U.S. patent application Ser. No. 11/492,425, filed Jul. 25, 2006, entitled "Warming Device", and published on Nov. 16, 2006 under Publication No. U.S. 2006/0259104;

U.S. patent application Ser. No. 11/583,432, filed Oct. 19, 2006, entitled "Multifunction Warming Device for Perioperative Use";

U.S. patent application Ser. No. 11/583,477, filed Oct. 19, 2006, entitled "Multifunction Warming Device with Provision for Being Secured";

U.S. patent application Ser. No. 11/583,480, filed Oct. 19, 2006, entitled "Multifunction Warming Device with Provision for Warming Hands"; and U.S. patent application Ser. No. 11/583,481, filed Oct. 19, 2006, entitled "Multifunction Warming Device with an Upper Body Convective Apparatus".

BACKGROUND OF THE INVENTION

A warming device that may be used perioperatively includes a clinical garment and convective apparatus with multiple sections supported on the inside of the garment. The sections are for receiving and distributing warmed, pressurized air and then circulating the distributed air through permeable surface areas. The permeable surface areas include areas of different permeability.

Convective devices that transfer heat to a human body are known. For example, there are devices that receive a stream of warmed pressurized air, inflate in response to the pressurized air, distribute it within a pneumatic structure, and emit the warmed air onto a body. These devices are typically called "convective thermal blankets" or "covers". Arizant Healthcare Inc., the assignee of this application, makes and sells such thermal blankets under the BAIR HUGGER® brand. One such device is the Model 522 Upper Body Blanket.

Use of the term "convective" to denote the transfer of heat between a warming device and a body refers to the principal mode of heat transfer, it being understood that heat may at the same time be transferred between a convective warming device and a body by conduction and radiation, although not to the degree of convection.

Convective warming has been used with increasing frequency to prevent or mitigate hypothermia during medical treatment. However, with the expansion of convective warming to treat core body cooling, it becomes apparent that it has manifold medical uses.

For example, a recent invention disclosed in the referenced PCT application adapts a clinical garment such as a robe or gown to receive a convective warming device in order to warm a person wearing the garment in a clinical setting for comfort and mobility of the person. Arizant Healthcare Inc., the assignee of this application, makes and sells such warming devices under the BAIR PAWS® brand. These devices are intended to warm patients prior to surgery, and there is a need to further adapt such a combination for use perioperatively.

The term "perioperative" is defined in the *PDR Medical Dictionary*, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. *AANA Journal.* 4/99;67,2:155–164.), therapeutic warming is employed during at least the intraoperative period in order to prevent or mitigate a constellation of effects that result from hypothermia. In fact, it is increasingly manifest that maintenance of normothermia perioperatively enhances the prospects for a quick, successful recovery from surgery. The effectiveness of therapeutic warming depends upon delivery of enough heat to a patient's body to raise the patient's core body temperature to, or maintain it within, a narrow range, typically near 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect. And conversely, there may be a secondary or ancillary therapeutic effect derived from the application of thermal comfort treatments such as the relief of patient anxiety. Thermal comfort is a subjective notion; however, the environmental conditions necessary to produce a sense of thermal comfort in a population of human beings are known and well tabulated. For example, Fanger (*Thermal Comfort: Analysis and Applications of Environmental Engineering.* Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Thermal blankets are typically used for therapeutic heating. An example is found in U.S. Pat. No. 6,524,332, "System and Method for Warming a Person to Prevent or Treat Hypothermia", commonly owned with this application. Thermal blanket designs have converged on a lightweight inflatable structure made of a flexible material which distributes warmed pressurized air over or against a permeable blanket surface that faces some portion of a patient's body and emits the distributed heated air through small apertures or interstices in the surface.

Thermal blanket design has been adapted for comfort warming by convective means such as those described in the referenced U.S. patent applications, and the referenced Publication No. WO 03/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced air warming unit, a heater unit, etc.), a convective device such as a thermal blanket (which is, typically, inflatable), and a flexible conduit or air hose connecting the heater/blower unit with the thermal blanket. Use of such a system for a particular type of warming requires delivery of warmed air through a convective device at parametric values that achieve a particular objective. The conditions by which a convective device produces thermal comfort in normothermic individuals at steady state are significantly different from those necessary to treat hypothermia. Typically the conditions for thermal comfort are met in a system with a relatively low capacity heater/blower unit, while those in a therapeutic warming system are achieved with a relatively high capacity heater/blower unit. The different capacities have led to use of air hoses with different capacities, with those delivering air flow for thermal comfort typically having smaller diameters than those serving a therapeutic warming requirement. The result is a divergence of designs leading to installation of different air delivery infrastructures for therapeutic and comfort warming.

Health care cost is an issue of national importance. The cost of warming perioperatively by convection is directly related to the number of perioperative periods in which a person is warmed; the cost increases when different convective warming apparatus are used in different periods to accomplish different goals. For example, when comfort and mobility are objectives of warming a person during the preoperative period and therapy is the objective of warming during one or more of the intraoperative and postoperative periods, it is presently necessary to use different convective warming configurations. Manifestly, if one convectively-operating warming device could be used or adapted to be used perioperatively, significant savings in thermal care could be realized.

SUMMARY

In one aspect, a warming device suitable for use perioperatively includes a clinical garment having an inside surface supporting a convective apparatus with multiple sections. At least one section is adapted for comfort warming and at least another section is adapted for therapeutic warming. The sections are provided to receive and distribute warmed, pressurized air and then emit the distributed air through a permeable surface. The surface includes areas of different permeability. The section adapted for comfort warming primarily includes areas of relatively low permeability; the section adapted for therapeutic warming primarily includes areas of relatively high permeability.

In another aspect, a warming device that may be used perioperatively includes a clinical garment and interleaved convective apparatus in an integrated structure attached to the inside of the garment. The interleaved convective apparatus are provided to receive and distribute warmed, pressurized air and then expel the distributed air through a permeable surface with regions of different permeability.

BRIEF DESCRIPTION OF THE DRAWINGS

FIGS. 4A and 4B are plan views of a surface of the convective apparatus through which air is expelled.

SPECIFICATION

A warming device that may be used perioperatively is constituted of a clinical garment and a convective apparatus with multiple sections supported on an inside surface of the garment. In this regard, a "clinical garment" is a garment that is typically used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. The convective apparatus has multiple sections, preferably two separate sections. Each section may receive and distribute at least one stream of warmed pressurized air in a pneumatic structure and emit the air through at least one permeable surface to thereby convectively warm a person wearing the clinical garment. Preferably the sections emit the air through respective sections of the same permeable surface. One section is adapted for comfort warming by convection, the other for therapeutic warming by convection. The permeable surface includes areas of different permeability.

In one aspect, a warming device capable of perioperative use may be worn on a person where it receives a first stream of warmed pressurized air in one section of the convective apparatus, distributes the pressurized air within the one section, and emits the air through a permeable surface of the one section to convectively warm the person's body for comfort. In another aspect, a warming device capable of perioperative use may be worn on a person where it receives a second stream of warmed pressurized air in the other section of the convective apparatus, distributes the pressurized air within the other section, and emits the air through a permeable surface of the other section to convectively warm the person's body for therapy. Preferably, the permeable surfaces are respective sections or regions of the same surface.

In this warming device, the sections emit air through surfaces or surface regions of varied or different permeabilities. Thus a section may emit air through a surface with a permeability that varies over the section or that is constant over the section but different than the permeability or permeabilities of a surface through which the other section emits air.

In the warming device illustrated and discussed below, each of the sections of the convective apparatus is inflatable. That is, the structure of each section, flaccid when not in use, tautens when receiving a stream of pressurized air.

Figure 1:
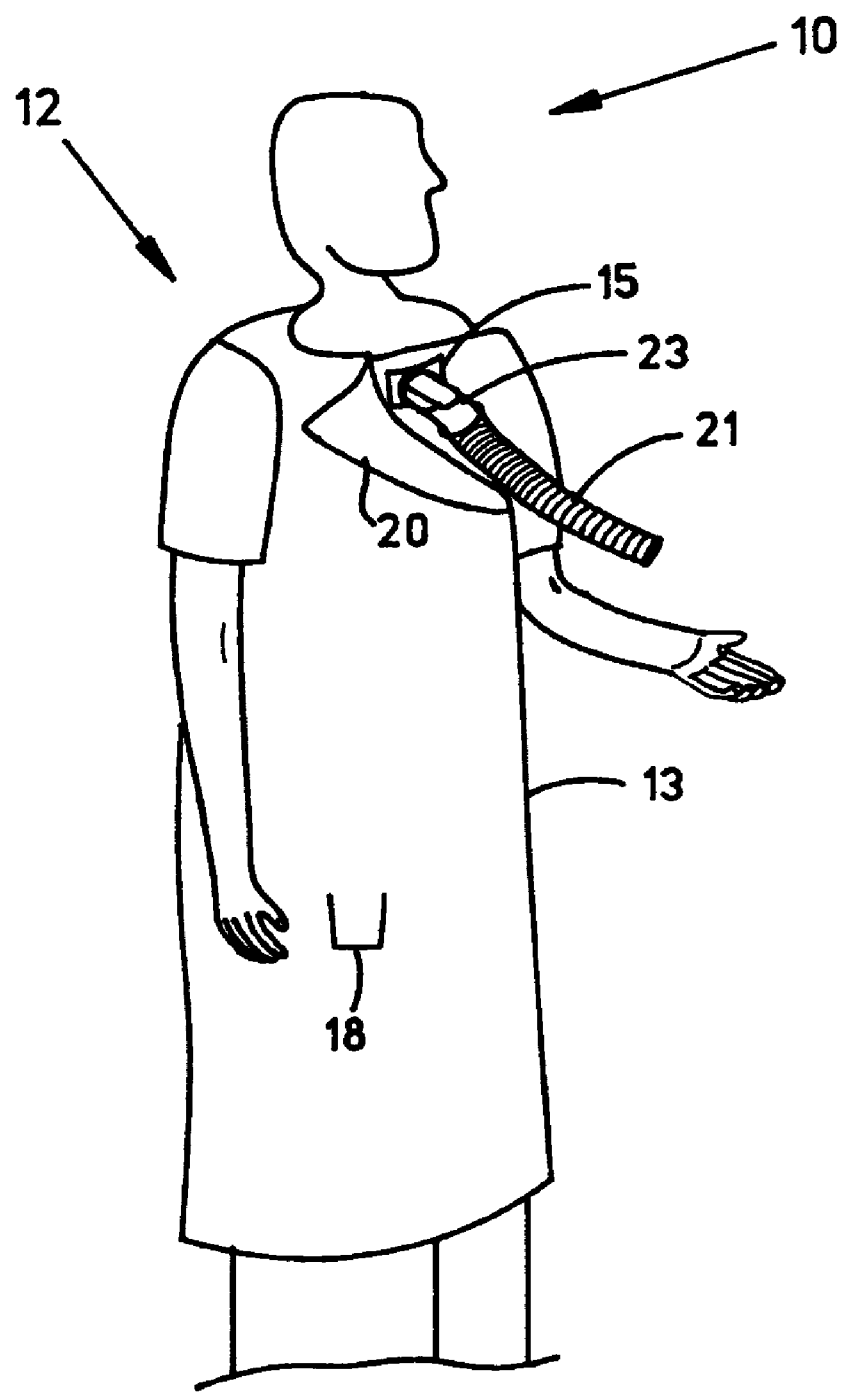
FIG. 1 is an illustration of a person wearing a warming device constituted of a clinical garment and a convective apparatus with multiple sections and a surface with varying permeability mounted to the inside of the garment.

Refer now to FIG. 1 in which a person 10 wearing a warming device 12 that may be used perioperatively is shown. The warming device 12 is constituted of a clinical garment 13 and a convective apparatus 15 with multiple sections that is supported on an inside surface of the clinical garment 13. The convective apparatus has for example two separate sections, each of which has at least one inlet port through which the section may receive warmed pressurized air from a heater/blower unit (not seen). Each inlet port is accessible through an aperture in the clinical garment 13. For example one inlet port for one of the sections may be accessed through a flap 18 in the clinical garment. An inlet port of another section may be accessed by releasing and folding down a portion 20 of the clinical garment. This latter form of access is illustrated in FIG. 1 where an air hose 21 with a nozzle 23 is received in an inlet port of one section of the convective apparatus 15. In this case, the portion 20 of the clinical garment comprises a portion of the upper edge and left sleeve that may be held to an opposing portion of the clinical garment by opposing strips of hook-and-eye material. Of course, this other inlet port may also be accessed through a flap such as the flap 18 instead of a folded-down garment section. Yet another means of accessing the inlet port for the other section would be to provide perforations in the nearest sleeve.

Convective apparatus such as thermal blankets have been specifically designed for particular uses. For example, a full body thermal blanket is adapted to lie upon the person and to extend longitudinally along the body of the person in order to cover substantially the person's entire body, from near the ankles or feet up to the neck. A lower body thermal blanket is adapted to lie upon the person and to extend longitudinally along the body of a person in order to cover the person's lower body, from near the ankles or feet up to the waist or pelvis of the person. An upper body thermal blanket has a bow-tie shape that is adapted to lie upon and extend transversely across the upper body of a person in order to cover the person's chest and extended arms. When fed a stream of warmed pressurized air, each of these thermal blankets inflates and distributes the air within itself. The pressurized air flows through apertures on a permeable surface of the thermal blanket which faces the person. These thermal blankets may have one, two, or more inlet ports through which an air hose provides warmed pressurized air from a heater/blower unit. The construction of thermal blankets is well understood. Examples of specific constructions are given in U.S. Pat. Nos. 5,620,482, 5,443,488, 5,360,439, and 5,304,213.

Typically, convective warming products are designed to provide a single mode of warming. Each of the thermal blankets described above is designed for therapeutic warming. The devices described in publication WO 03/086500 are designed for comfort warming. In contrast, the warming device described in this specification may provide either therapeutic warming or comfort warming, depending on the need. One section of the convective apparatus is constructed to receive air at low flow rates in order to provide comfort heating at steady state. Another section is constructed to receive air at higher flow rates in order to provide therapeutic heating at steady state.

Figure 2A:
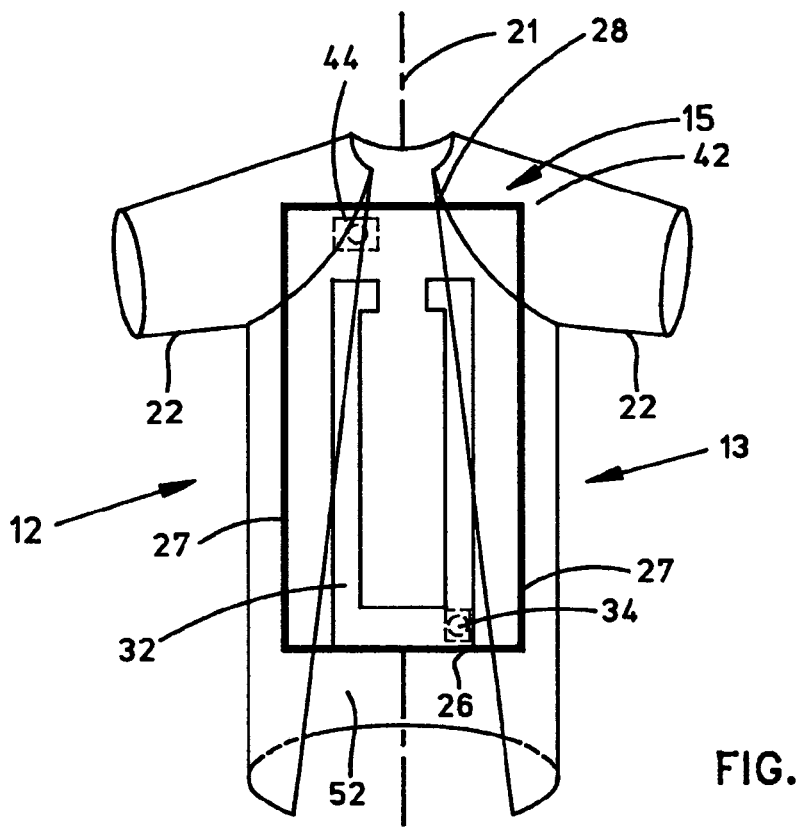
FIGS. 2A and 2B illustrate plan views of the warming device.
Figure 2B:
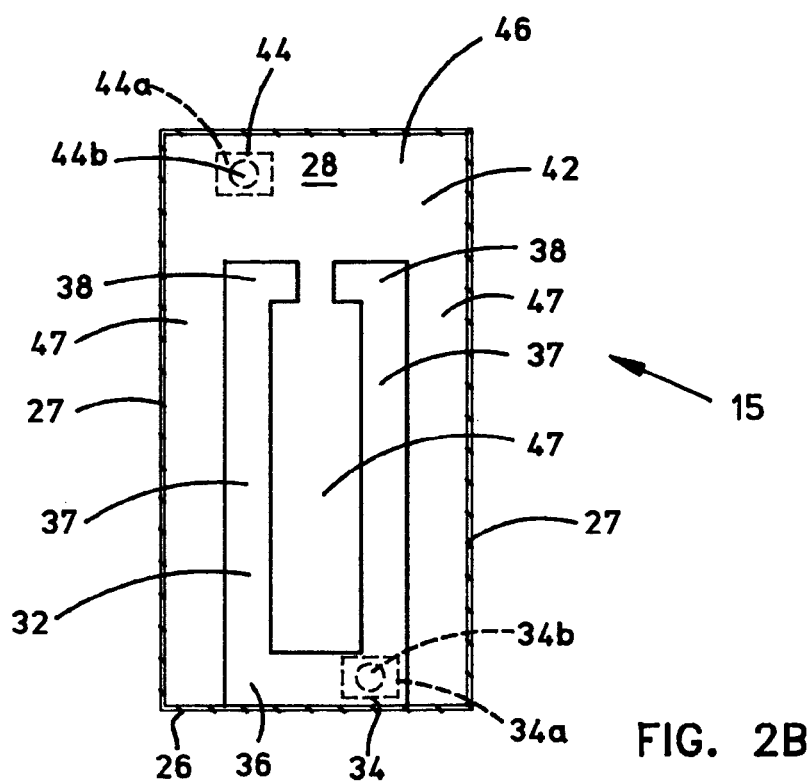

A convective apparatus 15 with multiple sections is illustrated in FIGS. 2A and 2B. In FIG. 2A the convective apparatus 15 is shown disposed inside the outline of the clinical garment 13; in FIG. 2B, the convective apparatus 15 is shown in plan view looking toward a permeable surface of the convective apparatus 15. The convective apparatus 15 has a quadrilateral shape with a base 26, sides 27 and top 28 which is perpendicular to the base 26. The base 26 and top 28 are centered on and extend transversely across a longitudinal axis 21 of the clinical garment 13, between the sleeves 22 of the clinical garment 13.

The convective apparatus 15 has multiple sections. A "section" of the convective apparatus 15 is a portion or division of the convective apparatus 15 that may be inflated and operated separately from any other section of the convective apparatus 15. For example, the convective apparatus 15 has a section 32 and a section 42. The section 32 may be inflated and operated separately from the section 42, and the section 42 may be inflated and operated separately from the section 32.

The section 32 has an inlet port 34, an elongate transverse part 36, and a pair of elongate parts 37 with lower ends that perpendicularly join respective ends of the transverse part 36. The upper ends of the two elongate parts 37 transition to transverse elongations 38. All together, the parts 36, 37, and 38 form a stylized "U". Although one inlet port 34 is illustrated in the section 32, one or more additional inlet ports may be provided for convenience. Unused inlet ports are sealed or closed by known means to prevent air escaping therethrough. Preferably the inlet port 34 is provided through the side of the convective apparatus 15 which is not visible in this figure; it may also be provided through an edge of the convective apparatus 15. The inlet port 34 may comprise a collar 34a of stiff material with an opening 34b to receive the nozzle of an air hose, or it may comprise a sleeve of material, or any other equivalent structure. The space in the transverse part 36 is in fluid communication with the spaces in the elongate parts 37 and the transverse elongations 38 so that pressurized air flowing through an inlet port into the transverse part 36 flows also into the elongate parts 37 and transverse elongations 38, thereby inflating the section 32. The surface of the section 32 which is visible in FIGS. 2A and 2B including the surfaces of the transverse part 36, the elongate parts 37, and the transverse elongations 38 is permeable, permitting pressurized air that is flowing into and inflating the section 32 to be expelled toward the interior of the clinical garment 13. The permeability of the surface of the section 32 may be constant or may vary as explained below.

The section 42 has an inlet port 44, an elongate transverse part 46, and a plurality of elongate parts 47 that connect perpendicularly to the transverse part 46. All together, the transverse part 46 and the elongate parts 47 form a comb structure. The elongate parts 47 of the section 42 are interleaved with the elongate parts 37 of the section 32, thereby forming an integrated convective apparatus 15 with dual sections. Although one inlet port 44 is illustrated in the section 42, one or more additional inlet ports may be provided for convenience. Unused inlet ports are sealed or closed by known means to prevent air escaping therethrough. Preferably the inlet port 44 is provided through the side of the convective apparatus 15 which is not visible in this figure; it may also be provided through an edge of the convective apparatus 15. The inlet port 44 may comprise a collar 44a of stiff material with an opening 44b to receive the nozzle of an air hose, or it may comprise a sleeve of material, or any other equivalent structure. The space in the transverse part 46 is in fluid communication with the spaces in the elongate parts 47 so that pressurized air flowing through an inlet port into the transverse part 46 flows also into the elongate parts 47, thereby inflating the section 42. The surface of the section 42 which is visible in FIGS. 2A and 2B, including the surfaces of the transverse part 46 and the elongate parts 47, is permeable, permitting pressurized air that is flowing into and inflating the section 42 to be expelled toward the interior of the clinical garment 13. The permeability of the surface of the section 42 may be constant or may vary as explained below.

The inlet port 34 of the section 32 has a smaller opening 34b than the opening 44b through the inlet port 44 of the section 42. Consequently, the inlet port 34 accepts an air hose nozzle with a smaller diameter than the air hose nozzle diameter accepted by the inlet port 44. The smaller nozzle diameter signifies a comfort warming air supply with an air hose having a smaller diameter than the air hose of a therapeutic warming air supply. Further, the smaller air hose may be coupled to a heater/blower unit with a smaller capacity than that of the heater blower unit of the therapeutic warming air supply. The smaller-diameter, smaller-capacity comfort warming air supply ensures that the section 32 operates in response to a heater/blower unit designed for comfort warming, while the larger-diameter, higher-capacity therapeutic air supply ensures that the section 42 operates in response to a heater/blower unit designed for therapeutic warming.

Figure 3A:
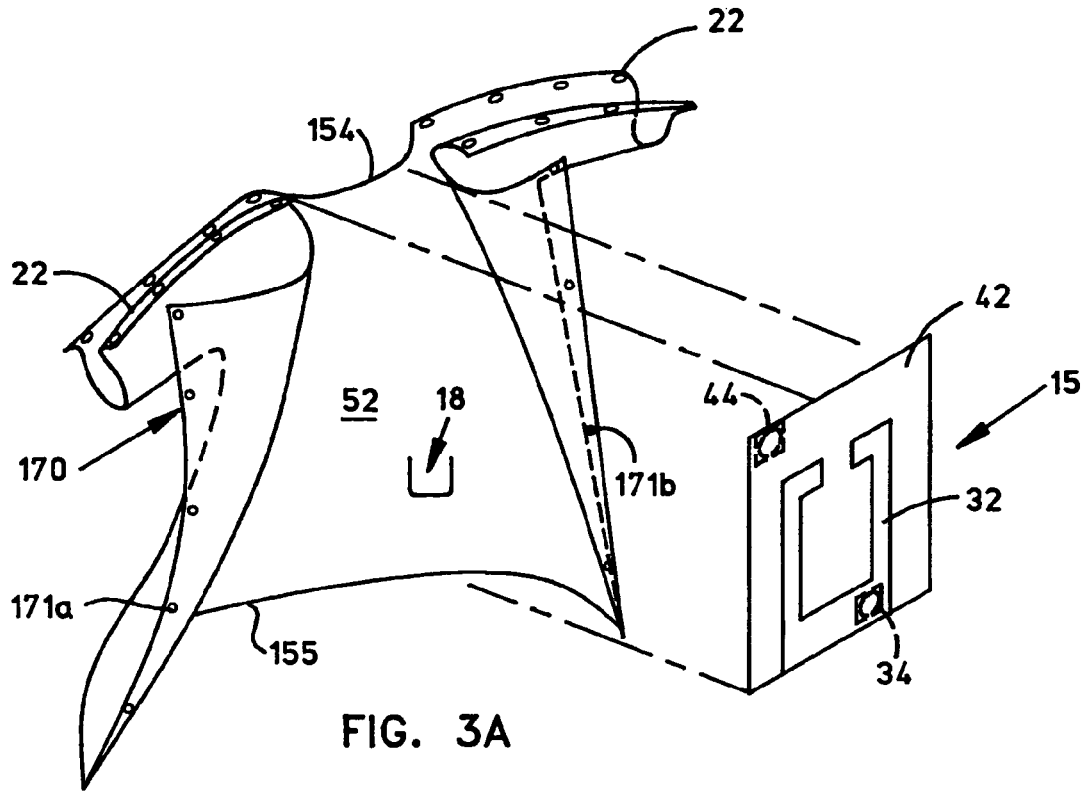
FIGS. 3A and 3B illustrate progressive stages of assembly of the warming device.
Figure 3B:
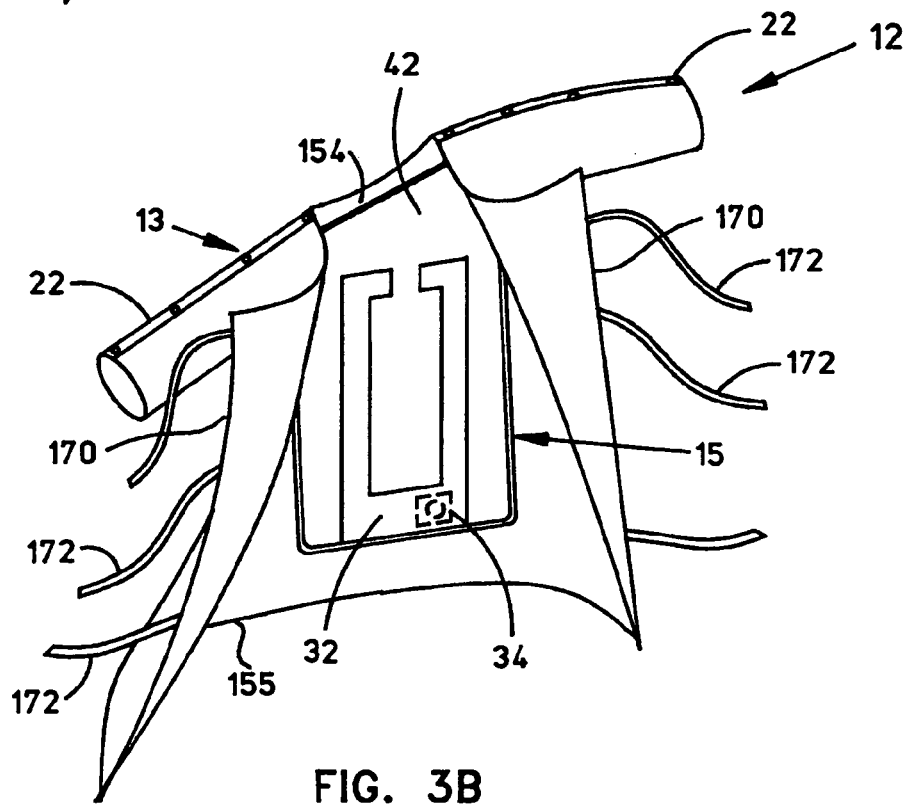

FIGS. 3A and 3B illustrate assembly of a warming device suitable for perioperative use constituted of the clinical garment 13 and the convective apparatus 15 with multiple sections. The convective apparatus 15 is adapted to be attached to, received on, supported on or constructed on the inside surface 52 of the clinical garment 13. The clinical garment 13 has at least one flap 18 through which an inlet port of one section may be accessed. For example, the flap 18 provides access to the inlet port 34 for receiving and retaining the nozzle of an air hose through which warmed pressurized air may be provided at a temperature and a capacity (in $ft^3$ per minute) to provide comfort warming for a person wearing the clinical garment 13.

Refer to FIGS. 2B, 3B, and 4B for an understanding of how the convective apparatus 15 may be constructed by joining two sheets of material, one permeable to permit warmed pressurized air to be emitted through the sheet, the other impermeable. With reference to FIGS. 2B and 3B, the impermeable sheet faces the clinical garment 13, while the permeable sheet faces the interior of the clinical garment 13. The convective apparatus 15 may be constructed as a separate piece and then attached to the inside surface 52 of the clinical garment 13 with the impermeable sheet against the inside surface 52 by tape, hook and eye material, snaps, or other equivalent structures. Alternatively, the convective apparatus 15 may be constructed integrally with the clinical garment by using a portion of the clinical garment itself as one of the sheets of the convective device. For example, with reference to FIGS. 2B and 4B two sheets 114 and 116 of flexible material are joined by a single substantially continuous seal 70 along the periphery of the convective apparatus 15, and also by continuous seal 72 that separates the sections of the convective apparatus and defines the parts of each section. Depending upon the materials selected, seals may be made for example by sewing, gluing, heating, or ultrasonically bonding the sheets along the seals, or by combinations thereof, or by any equivalent process.

Either or both of the sheets 114 and 116 may be a single sheet or may have a laminate structure. A laminate sheet structure may include a layer (114a, 116a) of extruded synthetic material lined with a layer (114b, 116b) of nonwoven material. If the permeable sheet has a laminate structure, holes or apertures 132 are formed through both layers 114a, 114b of the sheet 114 to provide a permeable surface through which warmed pressurized air can be emitted toward the interior of the clinical garment 13. In FIG.

4A, the sheets 114 and 116 are oriented to have the extruded layers (114a and 116a) facing, and the seals 70, 72 are formed by a gluing process or by a heating or ultrasonic process acting through one of the layers of non-woven material. Once constructed, the convective apparatus 15 may be attached to the inside surface 52 of the clinical garment by mechanisms 150.

In FIG. 4B, the sheet 114 may be a laminate structure as described above. If the clinical garment 13 is a woven cloth, such as cotton, or a non-woven such as spunbond-meltblown-spunbond material (SMS), the seals 70, 72 between the portion of the garment's inside surface 52 and the extruded layer of the laminate sheet may be formed by a gluing, a heating, or an ultrasonic process acting between the inside surface and the sheet 114.

Yet another alternative construction of the convective apparatus 15 is to construct the clinical garment 13 of a laminate sheet 116 and seal an apertured laminate sheet 114 or a single permeable layer 114b of woven or non-woven material thereto.

In yet another construction, the convective device may be constituted of an impermeable layer sealed around its periphery to the outside surface of the clinical garment so that the pneumatic structure is disposed on the outside of the clinical garment. In this case apertures are provided through the portion of the clinical garment beneath the impermeable layer.

Of course the sections of the convective device may be fabricated separately and placed on the inside surface 52 in the interleaved relationship shown in FIGS. 2A and 2B.

Examples of non-woven material include any one or more of polyester, cotton, rayon, polypropylene, and wood pulp. Examples of extruded synthetic material include polypropylene, polyesters, and polyurethanes. Polyolefin plastics, including polyethylene, may provide the best results in terms of manufacturability since both woven and extruded materials may be made from them. Examples of attachment materials and mechanisms 150 by which the convective apparatus 15 as presented in FIG. 4A can be attached to the inside surface 52 include two-sided adhesive, hook and loop, sewing, snaps, heat, ultrasonic, rivets, and any and all equivalents thereof.

Figure 5:
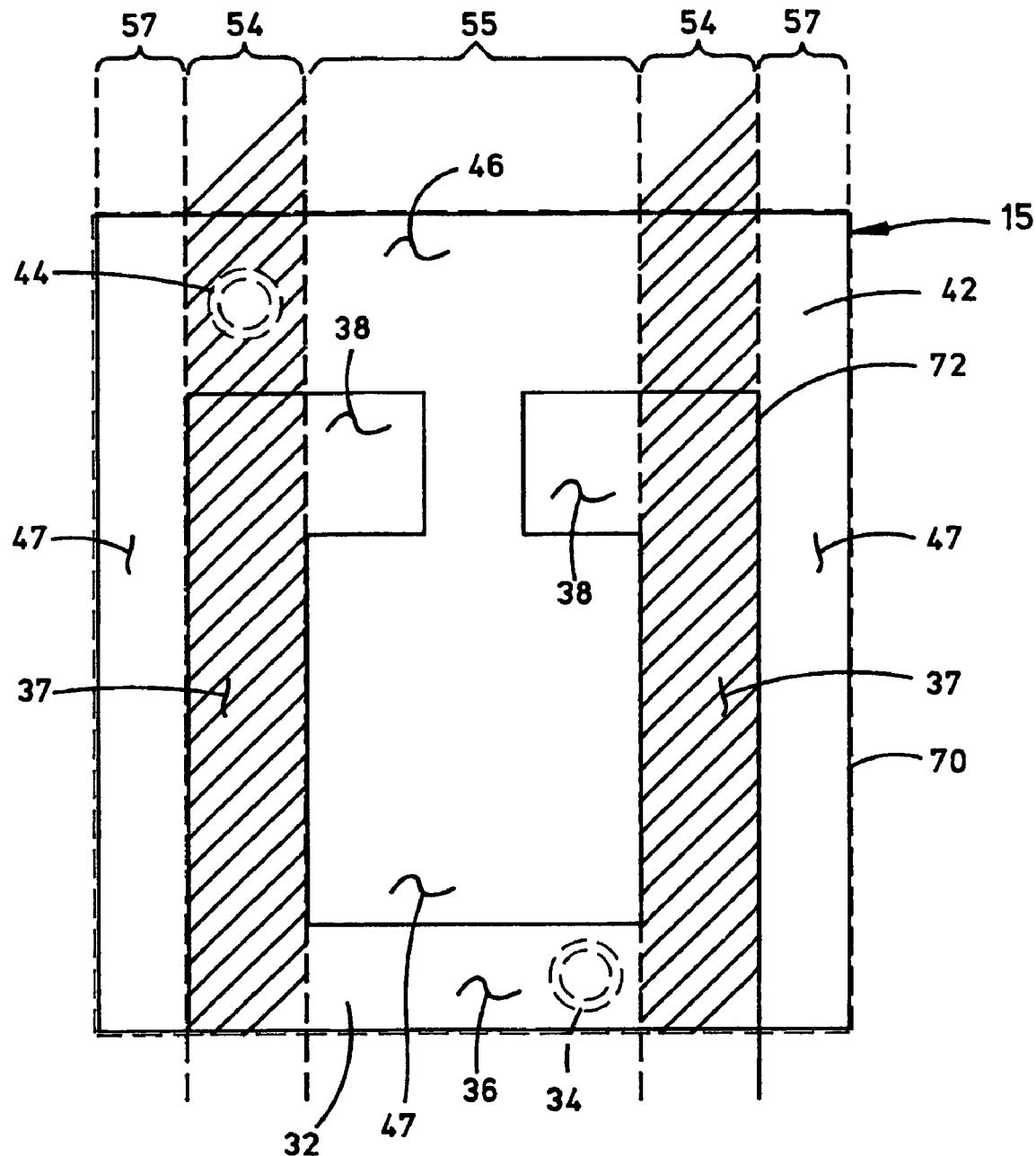
FIG. 5 is a plan view of the convective apparatus showing surface areas of varied or different permeability.

In this warming device, the permeability of the surfaces or surface portions of the sections through which air is emitted varies between the sections themselves. If desired, or if necessary to accommodate machines or processes with which convective devices are manufactured permeability may also vary within either or both sections. Preferably, the permeability of the surfaces of the section adapted for comfort warming is or is principally lower than the permeability of the section adapted for therapeutic warming. From another aspect, the permeability of the surfaces of the section adapted for therapeutic warming is or is principally higher than the permeability of the section adapted for comfort warming. Refer to FIG. 5 for an understanding of one example of varied permeability between the sections 32 and 42.

FIG. 5 is a plan view of the surface of the convective device 15 that faces the interior of the clinical gown 13. With reference to the exemplary construction shown in FIGS. 4A and 4B, the surface seen in FIG. 5 is the surface through which the sections 32 and 42 emit air in response to inflation. FIG. 5 is partly schematic and is intended to show not only features of the convective device 15, but also one way in which the exemplary convective device of FIGS. 4A and 4B may be manufactured.

In FIG. 5, the two parallel shaded strips 54 represent sections or regions of a first permeability, while the wide strip 55 between the strips 54 and the two parallel strips 57 outside the strips 54 represent sections or regions of a second permeability higher than the permeability of the shaded strips 54. (The shading in the strips 54 is used only to denote a value of permeability different from the value of permeability in the non-shaded strips). For clarity, the peripheral seal 70 and the seal 72 defining the first and second sections 32 and 42 are shown with respect to the strips 54, 55, and 57. As is evident, air is emitted from the parts 37 of the section 32 through regions having the permeability of the strips 54, which is lower than the permeability of the regions through which the transverse strip 36 and the transverse elongations 38 emit air. Further, the permeable regions through which the parts 47 and 46 emit air (with the exception of short portions of the strips 54) have the permeability of the strips 55 and 57, which is higher than the permeability of the strips 54. As a result, the mean value of permeability of the air-emitting region of the comfort section 32 is lower than the mean value of permeability of the air-emitting section of the therapy section 42.

In an aspect of the convective device shown in FIG. 5 which may be understood with reference to FIGS. 4A and 4B, the lower permeability in the strips 54 is provided by forming holes or apertures 132 in regions of a sheet corresponding to the strips with a first mean spacing between adjacent holes or apertures, for example, $\sqrt{2}$ inches. The higher permeability in the strips 55, 57 is provided by forming holes or apertures 132 in regions of a sheet corresponding to the strips with a second mean spacing between adjacent holes or apertures, for example, ½ inch. Manifestly, the greater spacing provides a density of holes or apertures that is lower than the density of the second spacing. This configuration is very convenient in a continuously-running web manufacturing process in which a web of material is punctured by a spiked roller with concentric circumferential bands of spikes that conform to the strips 54, 55, and 57.

Alternatively, permeability may be varied in a web configuration by providing different-sized spikes to form holes or apertures with uniform spacing but differing sizes. In this regard, smaller holes or apertures would be formed in the areas of lower permeability and larger holes or apertures in arrears of higher permeability. Of course, variation of both size and spacing of holes or apertures may be utilized to attain multiple patterns of variable permeability. In fact, generally, permeability variation may be realized in any manufacturing process capable of varying the size and/or density of the holes, apertures, interstices, ports, passageways of the material through which air is emitted in the described convective device. Such processes may include piercing the material and/or varying the composition or characteristics of the components of the material while the material is made.

One unanticipated advantage of the varied permeability pattern of FIG. 5 is that the sections 32 and 42 are enabled to reach similar inflation pressures while providing substantially different rates of emission. Another advantage of using varied permeability is that warmth can be focused or concentrated on certain body portions. For example, the section 32 has two distribution channels 37 with low permeability in fluid communication with the comfort regions 36 and 38 protruding into the high permeability area 55 in the center of the convective device 15. Presuming that the clinical garment 13 causes the convective device 15 to be disposed over, against, or in alignment with the center of a patient's body, a majority of the warmed pressurized air in the comfort section 32 will be emitted in these high permeability regions, thereby producing a heating effect focused on the upper thorax and legs of a patient. Further, effective warming is attained in both the clinical and therapeutic warming modes with the varied permeability configuration of FIG. 5. In this regard, the stylized U shape of the comfort section 32 at least partially encloses the central part 47 of the therapeutic section 42 while allocating most of the higher permeability in the center of the convective device to the therapeutic warming section 42, thereby providing sufficient heat transfer capacity for effective therapeutic warming to occur. However, enough of the high permeability in the central portion of the device 15 is allocated to the comfort section 32 to warm the center of a patient's body for comfort purposes.

As best seen in FIGS. 3A and 3B, the clinical garment 13 may be a standard gown, a modified gown or a special purpose gown. The gown may have a rear opening, a front opening or other suitable openings, such as a head opening in a poncho type gown. One type of gown shown in the figures has a rear opening. For example, in FIGS. 3A and 3B the gown 13 has a slit 170 that extends from the neck portion 154 to a hemline 155. A fastening means is provided for ease in securing the gown to the patient as well as allowing for ease in adjusting the size of the gown to accommodate various different-sized wearers. FIG. 3A shows one method using hook and eye buttons 171a, 171b positioned along opposing sides of the slit that can be brought together and fastened to hold the gown to the patient. Another method attachment shown in FIG. 3B is a plurality of strings 172 positioned along opposing sides of the slit 170 that can be tied together for holding the gown to a patient. Other methods of attachments include hook and eye elements, double-sided adhesive, snaps, rivets, and any and all equivalents thereof.

The clinical garment 13 may include sleeves 22 that are sized and positioned for receiving a patient's arms. Two examples of such sleeves 22 are shown in the figures. In FIGS. 3A–3B the sleeve portions are slit the entire length on the shoulder or top. This allows access to the upper body of the patient and the inlet port 44 and allows for opening and closing of the slit sleeves 22 in an adjustable fashion using buttons, snaps, repositionable adhesive, hook and eye elements, double-sided adhesive, hook and loop, rivets, and any and all equivalents thereof. The design shown in FIG. 3A also facilitates the manufacturing of the clinical garment 13 in one piece.

In use, a person is warmed perioperatively using a warming device constituted of a clinical garment and a dual-section convective apparatus supported on an inside surface of the clinical garment by dressing a person with the clinical garment during the preoperative period, coupling a first section (the section 32 in FIG. 2B, for example) of the convective apparatus to a source of warmed pressurized air for comfort warming, and convectively warming the person for comfort by way of the first section. To prepare for surgery, the first section is decoupled from the comfort warming source and the clinical garment is arranged to afford access to a surgical site. In preparation for surgery, the clinical garment may be left on the person, with its skirts rolled up to provide surgical access. Alternatively, the clinical garment may be removed to allow the convective apparatus to be positioned on the person to provide surgical access. In this latter case, the skirts, sleeves and other loose parts of the clinical garment may be rolled or folded onto the convective device. In yet another alternative, if the convective device is releasably attached to the inside surface of the clinical garment, the garment may be separated from the convective device during surgery and reattached later postoperatively. During surgery, the convective device may be secured to the person by means of the double sided adhesive and a second section of the convective apparatus (for example the section 42 in FIG. 2B) may be coupled to a source of warmed pressurized air for therapeutic warming, and the person may be convectively warmed for therapy by way of the second section. Following surgery, the convective apparatus is detached from the person (but only if secured to the person for surgery), the convective apparatus is reattached to the clinical garment (but only if detached therefrom for surgery), the person is again dressed with the clinical garment and either warmed for comfort or warmed for therapy.

Manifestly, the descriptions and illustrations in this specification are presented for an understanding of how to make and use an exemplary warming device. The only limitations on the scope of protection afforded the inventive principles presented are in the following claims.

The invention claimed is:

1. A warming device, comprising:
   a clinical garment with an inside surface; and
   a convective apparatus supported on the inside surface;
   the convective apparatus including a first section adapted to provide comfort warming by convection through a first permeable surface and a second section adapted to provide therapeutic warming by convection through a second permeable surface;
   the first permeable surface including a first region with a first permeability; and
   the second permeable surface including a second region with a second permeability greater than the first permeability;
   wherein the first and second sections are separately inflatable.

2. The warming device of claim 1, wherein the first section includes:
   a transverse part;
   a plurality of elongate parts extending from and in fluid communication with the transverse part; and
   at least one inlet port.

3. The warming device of claim 2, wherein the second section includes:
   a transverse part;
   a plurality of elongate parts extending from and in fluid communication with the transverse part; and
   at least one inlet port.

4. The warming device of claim 3 wherein the elongate parts of the first section are interleaved with the elongate parts of the second section.

5. The warming device of claim 3, wherein the first section has the shape of a "U".

6. The warming device of claim 5, wherein the second section has the shape of a comb.

7. The warming device of claim 1, further including at least one inlet port in each of the first and second sections.

8. The warming device of claim 7, further including an aperture in the clinical garment to an inlet port of the first section.

9. The warming device of claim 8, further including a portion of at least one sleeve of the clinical garment separable from a corresponding portion of the sleeve to provide access to an inlet port of the second section.

10. A warming device, comprising:
    a clinical garment with an inside surface; and
    a convective apparatus supported on the inside surface;

the convective apparatus including dual sections to provide comfort warming by convection through a surface having a first mean permeability and therapeutic warming by convection through a surface having a second mean permeability higher than the first mean permeability;

wherein the dual sections are separately inflatable.

11. The warming device of claim 10, wherein a first section includes:

a transverse part;

a plurality of elongate parts extending from and in fluid communication with the transverse part; and at least one inlet port.

12. The warming device of claim 11, wherein a second section includes:

a transverse part;

a plurality of elongate parts extending from and in fluid communication with the transverse part; and at least one inlet port.

13. The warming device of claim 12, wherein elongate parts of the first section are interleaved with elongate parts of the second section.

14. The warming device of claim 10, further including at least one inlet port in each of the sections.

15. The warming device of claim 14, further including an aperture in the clinical garment to an inlet port of the first section.

16. The warming device of claim 15, further including a portion of at least one sleeve of the clinical garment separable from a corresponding portion of the sleeve to provide access to an inlet port of the second section.

17. A warming device, comprising:

a clinical garment with an inside surface; and a convective apparatus supported on the inside surface;

the convective apparatus including two separately inflatable sections; and the convective apparatus including a permeable member shared by the sections for emitting air;

the permeable member having at least one region of low permeability in a first section and at least one region of high permeability in the second section.

18. The warming device of claim 17, wherein each permeable member faces the interior of the clinical garment.

19. The warming device of claim 18, wherein the first section includes:

a transverse part;

a plurality of elongate parts extending from and in fluid communication with the transverse part; and at least one inlet port.

20. The warming device of claim 19, wherein the second section includes:

a transverse part;

a plurality of elongate parts extending from and in fluid communication with the transverse part and interleaved with elongate parts of the first section; and at least one inlet port.

21. The warming device of claim 18, wherein the first section has a shape that partially encloses the at least one region of high permeability.

22. A method for warming a person perioperatively using a warming device constituted of a clinical garment and a dual-section convective apparatus supported on an inside surface of the clinical garment, comprising:

dressing a person with the clinical garment preoperatively;

coupling a first section of the convective apparatus to a first source of warmed pressurized air;

convectively warming the person for comfort by way of a surface of the first section having a first permeability decoupling the first section from the first source;

coupling a second section of the convective apparatus to a second source of warmed pressurized air; and convectively warming the person for therapy by way of a surface of the second section having a second permeability higher than the first permeability.

* * * * *

UNITED STATES PATENT AND TRADEMARK OFFICE
CERTIFICATE OF CORRECTION

PATENT NO. : 7,226,454 B2 Page 1 of 1
APPLICATION NO. : 11/005883
DATED : June 5, 2007
INVENTOR(S) : Thomas P. Anderson et al.

It is certified that error appears in the above-identified patent and that said Letters Patent is hereby corrected as shown below:

<u>Title Page, Page 2</u>
Under the heading FOREIGN PATENT DOCUMENTS, replace "WO 2006/010170" with --WO 2006/020170--.

Under the heading OTHER PUBLICATIONS, add --International Search Report & Written Opinion for PCT/US2005/043968, mailed April 19, 2006-- below the reference to "Porta-Chill—The Portable Air-Chiller-Brochure, http://www.portachil.com/, Dec. 3, 2002."

<u>Column 1, line 29</u>
Add opening quotation marks before the word "Multifunction".

<u>Column 1, line 30</u>
Add closing quotation marks after the word "Use".

<u>Column 1, line 42</u>
Delete the word "US" and replace it with --U.S.--.

<u>Column 11, line 23</u>
Add the words --to provide-- after the word "provided".

Signed and Sealed this

Eighth Day of July, 2008

JON W. DUDAS
*Director of the United States Patent and Trademark Office*